United States Patent [19]

Taguchi et al.

[11] Patent Number: 5,102,794
[45] Date of Patent: Apr. 7, 1992

[54] NOVEL SUBSTANCE FOR AGRICULTURAL USE

[75] Inventors: Ryusuke Taguchi, Yokohama; Hideo Sugawara, Toride; Yukio Miyazaki, Ageo; Taku Mizuno, Kamifukuoka; Masahide Nomura, Tokyo; Machiko Sugiyama, Kawaguchi; Hideo Saito, Kukizaki; Goro Yabuta, Tokyo; Akiya Furuichi, Kawasaki; Yasuhiko Hamazaki, Ushiku; Katsuhiro Nakamura, Tokyo, all of Japan

[73] Assignee: Kaken Pharmaceutical Co., Ltd., Tokyo, Japan

[21] Appl. No.: 640,867

[22] Filed: Jan. 14, 1991

Related U.S. Application Data

[62] Division of Ser. No. 320,599, Mar. 8, 1989.

[30] Foreign Application Priority Data

Mar. 11, 1988 [JP] Japan ............................ 63-58041

[51] Int. Cl.⁵ ........................ C12P 17/04; C12R 1/645
[52] U.S. Cl. ...................................... 435/126; 435/911
[58] Field of Search ............... 435/911, 126; 514/473; 549/322, 326

[56] References Cited

U.S. PATENT DOCUMENTS

4,804,676 2/1989 Inaoka et al. ..................... 435/121

FOREIGN PATENT DOCUMENTS

2538771 3/1977 Fed. Rep. of Germany ...... 514/473

OTHER PUBLICATIONS

Michael et al., "JACS", vol. 55 ∩9 9-1933, pp. 3684-3695 (pp. 3689 & 94).
Dewent Abs. 86-215126/33 (J61146188) Jul. 1986-Rikagaku.
Derwent Abs. 88-201162/29 (J63137696) Jun. 1988-Ajinomoto.
Derwent Abs. 87-238795/34 (J62161796) Jul. 1987 Fujisawa.
Derwent Abs. 86-340409/52 (EP-205981) Dec. 1986 Umezawa et al.

*Primary Examiner*—Herbert J. Lilling
*Attorney, Agent, or Firm*—Oblon, Spivak, McClelland, Maier & Neustadt

[57] ABSTRACT

Substance F-0368 of the formula:

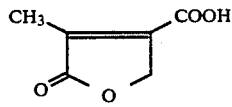

or salts thereof is prepared by culturing Kitasatosporia sp. F-0368 in a culture medium thereby producing substance F-0368, and then isolating and collecting substance F-0368 from the culture medium.

1 Claim, 2 Drawing Sheets

NOVEL SUBSTANCE FOR AGRICULTURAL USE

This is a division, of application Ser. No. 07/320,599, filed on Mar. 8, 1989.

This invention relates to a novel substance identified as "F-0368". More particularly, it is concerned with such "F-0368" substance useful as disinfectant for agricultural purposes; process for its production; agricultural chemical composition containing such substance; preventive agent for plant and vegetable diseases; disinfectant for agricultural use; materials for agricultural use; method for preventing diseases in agriculture using such disinfectant; method for growing plants using such disinfectant; and F-0368 substance producing microorganism.

As the preventive agent against rice blast disease, there have conventionally been known iso-protiolane, phthalide, IBP, probenazole, EDDP, and others; and, as the preventive agent against bacterial leaf blight disease, there have been known phenazine oxide, probenazole, organic nickel compounds, and others.

Since the above-mentioned conventional chemicals are unable to display their sufficient activity with a low dose, a relatively high dose of such chemicals have been practiced so far, on account of which high possibility of environmental pollutions in air, water, soil, and so forth have been apprehended, and also some of these chemicals were harmful to human being and animals.

Therefore, the present invention aims at providing a novel substance which exhibits sufficient activity with a low dose, and possess excellent preventive effect against various plant diseases such as, in particular, rice blast disease and bacterial leaf blight disease. Further, the present invention aims at providing process for production of such novel substance, agricultural chemical compositions containing therein such novel substance, preventive agent for plant and vegetable diseases by use of such substance, disinfectant for agricultural purposes using such substance, materials for agricultural purposes containing such substance, method for preventing diseases in agriculture using such disinfectant, method for cultivating plants using such disinfectant, and microorganism producing such novel substance.

With a view to searching out useful agricultural chemicals, the present inventors conducted research activities by separating a number of microorganisms from various soil, isolating substances produced by the microorganisms, and identifying the substances as obtained. As the result, they discovered that a strain of ray fungus identified as "F-0368" belonging to a genus Kitasatosporia as separated from a vegetable field in Nerima-ku, Tokyo, Japan had been able to accumulate in a culture medium a substance having excellent preventive effect against rice blast disease and bacterial leaf blight disease. Based on this finding, the present inventors isolated the substance produced by the microorganisms, and compared its physico-chemical properties with those of known substances, as the result of which they confirmed that the substance was new, which had not been identified hitherto, and thus completed the present invention.

This novel substance of "F-0368" according to the present invention has its physico-chemical properties as indicated below.

1) Structural Formula:

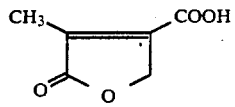

2) Melting point:
165° C. to 168° C. (measured by use of an automatic melting point measuring device "METLER FP1"); sublimating at a temperature ranging from 133° C. to 134° C. (measured by use of a thermal analysis device "SHIMADZU TG-30").

3) Solubility to Solvent:
Readily soluble in methanol, ethanol and acetone; Soluble in ethyl acetate and water; Non-soluble in chloroform, benzene and hexane.

4) Ultraviolet Ray Absorption Spectrum;
Indicating maximum absorption at 225 nm $\lambda max\ MeOh\ (E_1\ _{cm}\ 1\%) = 225\ nm\ (1070)$ 5) Distinction Among Basic, Acidic and Neutral:
Acidic substance 6) Color Rendering Reaction:
Positive: potassium permanganate
Negative: iodine iode, ninhydrin, ferric chloride, and 2,4-dinitrophenylhydrazine 7) Elemental Analyses:

|  | C | H | O |
| --- | --- | --- | --- |
| Measured Value (%) | 50.63 | 4.25 | 45.10 |
| [Theoretical Value (%)] | 50.70 | 4.22 | 45.07 |

8) Infrared Ray Absorption Spectrum:
Infrared ray spectrum measured by the KBr method 3000, 2740, 2640, 2520, 1730, 1670, 1450, 1430 1380, 1360, 1210, 1150, 1110, 1020, 890, 880, 760, 710 $(cm^{-1})$ 9) Nuclear Magnetic Resonance Spectrum (60 MHz):
$\delta(ppm)$
Measurement carried out in heavy methanol $d_6$-DMSO 2.05(3H, t), 4.85(2H, q), 11.33(1H, s)

As is apparent from the above physico-chemical properties, the "F-0368" substance according to the present invention proves to be an acidic substance, hence it can be modified into a salt form. Examples of the salt are as follows: alkali metal salts such as sodium salt, potassium salt, lithium salt, and so on; alkaline earth metal such as calcium salt, magnesium salt, and so forth; ammonium salt; organic salts such as triethylammonium salt, and others; and complex salts of iron, copper, cobalt, and so forth.

The substance "F-0368" according to the present invention can be produced from a strain of microorganism belonging to a genus Kitasatosporia which is capable of producing the substance "F-0368".

As one example, the present inventors isolated from soil in a vegetable field at Nerima-ku, Tokyo, Japan a actinomycetes belonging to a genus Kitasatosporia having the following mycological properties, and they gave this strain or microorganism a nomenclature of Kitasatosporia sp. F-0368. This strain was deposited on Jan. 28, 1988 with Fermentation Research Institute, Agency of Industrial Science and Technology, Ministry of International Trade and Industry, 1-3, Higashi 1-chome, Yatabe-machi, Tsukuba-gun, Ibaraki-ken 305, Japan, and assigned a deposit number of "FERM P-9845", which was transferred to an international deposition on Jan. 26, 1989 under "FERM BP-2259".

The natural and artificial mutant strains of the above-mentioned strain of Kitasatosporia sp. F-0368 belongs, as a matter of course, to the genus Kitasatosporia. Therefore, all the microorganisms capable of producing the substance "F-0368" according to the present invention can be used, without exception, for the purpose of the present invention, hence they are included in the strains to be used in the present invention.

The mycological properties of the strain "F-0368" which produces the substance "F-0368" according to the present invention are as follows.

(I) Morphological Properties

The strain of the actinomycete "F-0368" to be used in the present invention has a branched mycelium, of which the aerial mycelium extending in the air is frag- Using various culture media, the properties of the strain "F-0368" were examined. The experiments were conducted in accordance with the method as reported by E. B. Sharring et al. ("International Journal of Systematic Bacteriology", Vol. 16, pp.313 to 340, 1966), with additional use of the well known culture media and experimental methods. The color tone was determined by use of "Color Harmony Manual", 4th Ed., by Container Corp.)"as a standard color chart under a standard light source with a xenon lamp as the source of light, wherein, if a coincident color chart is found, a generic name is shown first and a color chart code is subsequently shown together in a parenthesis. Unless otherwise specified hereinafter, growth of the strain in the culture medium was carried out in an agar plate culture for three weeks at a temperature of 28° C. The detailed results of the experiments are indicated in Table 1 below.

TABLE 1

| Culture medium | Growth | Aerial mycelium | Color of aerial mycelium | Color of substrate mycelium | Soluble pigment |
| --- | --- | --- | --- | --- | --- |
| sucrose-nitrate-agar medium (Difco, Czapek solution agar) | poor | poor to moderate | 2db (ivory) | none | none |
| glucose-asparagine-agar medium | moderate | good sparse | 7ba~10dc (pink tint~ orchid haze) | 4ic (pastel orange suntan) | none |
| glycerol-aspartate-agar medium (Difco, ISP-5) | poor | moderate sparse | 2db (ivory) | 13ba (alabaster tint) | none |
| starch-agar medium (Difco, ISP-4) | good sparse | abundant | 5fe (ashes) | 3ni (clove brown) | none |
| nutrient agar medium | moderate slightly good | none | none | 2fb (bamboo) | none |
| tyrosine agar medium (Difco, ISP-7) | moderate | moderate (cottony) slightly sparse | 10cb (orchid mist) | 3le (yellow maple) | none . |
| yeast-malt-agar medium | abundant | abundant | 5fe (ashes) | 3pl (deep brown covert brown) | none |
| oat meal-agar medium | poor~ slightly moderate | good | 13cb (pearl grey) | 2ca (light ivory egg shell) | none |
| yeast starch agar medium | moderate~ good sparse | good sparse | 10dc (orchid haze) | 2nl~3gc (covert brown~ light tan) | none | mented and its terminal end forms a long chain of spores in number ranging from 5 to 20. The strain exhibits particularly favorable growth and formation of spores in a starch-agar medium, yeast-malt-agar medium, and yeast-starch-agar medium. Its substrate mycelium assumes yellowish brown to brown in color, its aerial mycelium assumes white to gray in color. Observation through an electron microscope reveals that the terminal end of the spore which has been branched with respect to the principal axis indicate a rectus-flexibilis form, and, in a rare occasion, it shows a hook form. The spore has a smooth surface or an irregular rugose surface. It is cylindrical or elliptical in form with a dimension of 3 μm–4 μm × 1.7 μm–2.0 μm. No sporangium, sclerotium, and coremium were observed.

(II) Cultural Characteristics

III) Physiological Properties

Temperature range for growth (growth as at the end of the second week in the maltose-Bennet-agar medium, at a pH value of 7.3 before sterilization and using a temperature gradient apparatus)

Appropriate temperature . . . 19.2° C. to 36.2° C.

Growable temperature . . . 14.0° C. to 42.3° C.

2) Liquefaction of gelatin (stab culture in glucose-peptone-gelatin medium)

20° C.: nagative

27° C.: pseudo-positive

3) Coagulation and peptonization of milk (Difco, skim milk medium at 28° C. and 37° C. respectively)

28° C. peptonized: positive, coagulation: negative

37° C. peptonized: positive, coagulation: negative

4) Formation of melanine tyrosine-agar medium: negative
melanine forming medium: negative
peptone-yeast-iron-agar medium: negative
tripton-yeast-liquid medium: negative 5) Dissolution of adenine, xanthine, hypoxanthine, and tyrosine adenine, xanthine, and tyrosine negative hypoxanthine: positive 6) Salt resistance (in maltose-Bennet agar medium+NaCl at 28° C.) Growth observed upto 2% of the medium (no growth seen at 3%)

7) Capability of utilizing carbon source (in Difco, carbon utilization agar medium at 28° C., at the end of second week)
   positive: D-glucose, L-arabinose, D-xylose, rhamnose, salicin
   negative: sucrose, D-fructose, raffinose, i-inositol, D-mannitol (IV) Chemical properties From hydrolyte of the whole cells, both LL-diaminopimelic acid and meso-diaminopimelic acid were detected.

From the aerial mycelium on the agar plate, a large amount of LL-diaminopimelic acid was detected, but mesodiaminopimelic acid was detected only slightly.

As the sugar component, there were detected galactose and mannose. The principal menaquinone is MK-9 ($H_6.H_8$). The fatty acid composition is of a branched type. The acyl type of the amino group in the muramic acid is the acetyl type.

As described in the foregoing, the strain of microorganism F-0368 according to the present invention has been identified as belonging to the genus Kitasatosporia, since it possesses the genuine branched mycelium; the aerial mycelium extending into the air is fragmented to form a long chain of spores; the amino acid composition in the whole cells contains both LL-diaminopimelic acid and meso-diaminopimelic acid; a large quantity of LL-diaminopimelic acid is detected from the analysis of diaminopimelic acid in the aerial mycelium; and the menanoquine component is principally made up of MK-9 ($H_6.H_8$), hence the strain of microorganism was identified as Kitasatosporia sp. F-0368.

The substance F-0368 according to the present invention can be produced by culturing an F-0368-producing-microorganism belonging to the genus Kitasatosporia such as, for example, Kitasatosporia sp. F-0368 in a culture medium containing nutritive substances which can be usually availed by the microorganism, and by isolating and extracting the substance F-0368 from the culture broth. Examples of the nutritive substances which can be used for the purpose of the present invention are: (i) as the carbon source, glucose, glycerol, sucrose, dextrin, starch, and so on; (ii) as the nitrogen source, soybean meal, wheat embryo, peptone, eat extract, yeast extract, corn steep liquor, ammonium salt, and so forth. Besides these substances, there may be used, depending on necessity, calcium carbonate, potassium chloride, magnesium sulfate, phosphates, and other inorganic salts.

As the method for culturing the microorganism, the liquid culture method is suitable. The culturing conditions such as temperature, time, and others are so selected that they may be adapted for the growth of the microorganism used, and yet production of the substance F-0368 may become maximum. For instance, the culturing is carried out under an aerobic condition, and the cultivating temperature ranges from 25° C. to 35° C., or it may perferably be 28° C. When the culturing is carried out under aeration and agitation for a time period of from 92 to 144 hours, production of the substance F-0368 reaches its maximum.

For isolating and purifying the substance F-0368 produced and accumulated in the culture broth, various methods which are usually employed may be appropriately selected and used. For example, a method of utilizing difference in solubility between the cultivated substance and impurities, a method of utilizing difference in functional groups of compounds such as anion exchange resin, and a method of utilizing difference in adsorptive affinity of silica gel, DIAION HP-20 (a tradename for a product of Mitsubishi Kasei Corporation, Japan) and so forth can be used singly, or in combination, or in repetitive manner.

Verification of the active portion of the cultured substance can be done by means of a silica gel thin layer chromatography (TLC).

One example of the method for isolating and purifying the substance F-0368 is as follows: that is to say, while the substance F-0368 is also present in the mycelia, it exists principally in the filtered liquid of the culture; accordingly, the mycelia is first removed by filtration or centrifugal separation with addition of a filtration auxiliary to the culture broth, then the thus obtained culture liquid is rendered acidic (pH value of 2) with use of hydrochloric acid, and any coloring matters are eliminated by means of a column chromatography of adsorbing resin (DIAION HP-20), to thereby elute the active substance.

Further, this active portion is collected and extracted by use of ethyl acetate, in utilizing the property of organic solvents which is soluble under acidity. Then, the extracted solution is cencentrated under a reduced pressure, whereupon a crude extract of the substance F-0368 is obtained.

Subsequently, this crude extract is subjected to purification process by means of an adsorbing chromatography such as silica gel column chromatography to collect the active portion, which is then concentrated and dried. As the result, there will be obtained crystals of the substance F-0368 in the form of a free acid.

Furthermore, the crystal in the free acid form as isolated can be modified into the form of various salts by the conventional expedients.

As another method, the following synthetic method is also able to produce the substance F-0368 according to the present invention.

3-methyl-4-lower alkoxy carbonyl-2(5H)-furanone [prepared by the method of synthesis as described in "Tetrahedron, 31, (15) 1659" by S. W. Pelletier et al.] represented by the following general formula was dissolved in, for example, water or a mixture of water and an alcohol such as methanol, ethanol, etc. in the presence of a solvent such as hydrochloric acid, sulfuric acid, tosylic acid, methanesulfonic acid, etc., and then the batch is subjected to reaction for a time period of from 1 to 24 hours in general at a room temperature to 100° C., whereupon the substance F-0368 as the end product can be obtained.

[General Formula]

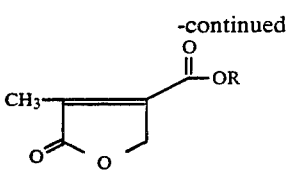

The substance F-0368 according to the present invention possesses sufficient preventive activity with a low dose, and exhibits excellent preventive effect against the rice blast disease and the bacterial leaf blight disease.

That is to say, as the result of the experiments for preventing the rice blast disease, the substance F-0368 according to the present invention exhibited not only such preventive effect by its spraying on the surface of leaves, but also indicated very excellent preventive effect, in particular, in the experiments of soil treatment and spraying on the water surface. Also, the substance exhibited excellent preventive effect against the bacterial leaf blight disease which is a bacterial disease of rice plant through its spraying on the water surface.

Such high activity of the substance F-0368 according to the present invention not only by its spraying on the surface of plant leaves, but also by the soil treatment and its spraying on the water surface proves that the substance possesses its remakable preventive effect.

Moreover, the excellent preventive effect exhibited by the substance F-0368 according to the present invention against the rice blast disease which is the disease of the rice plant due to the fungi, and against the bacterial leaf blight disease which is the disease of the rice plant due to bacteria is a very peculiar phenomenon.

Incidentally, in its concentration of 500 μg/ml, the substance F-0368 did not indicate its anti-microbial activity in vitro with respect to bacteria, yeast, and filamentous fungi.

Further, the substance F-0368 has low acute toxicity against mice, with the consequence that the substance is less harmful to human being and animals, hence it is highly excellent as the disinfectant for agricultural use.

As the disinfectants for agricultural use according to the present invention, which contain therein, as the active component, the substance F-0368 and/or its salts, there may be enumerated the following examples (1) disinfectants, in which the substance F-0368 is used as it is; (2) disinfectants obtained by diluting the substance F-0368 with use of water, solid powder, or other appropriate carries, and, depending on necessity, adding an adjuvant such as spreading agent, etc.; or (3) various disinfectant formulations prepared by those methods which are generally adopted in the production of agricultural chemicals, wherein the substance is mixed with various liquid or solid carries, and, if necessary, it is added with auxiliaries such as wetting agent, spreading agent, dispersing agent, emulsifier, binder, and so forth, thereby preparing the substance in the form of water-dispersible powder, liquid, water-soluble powder, sol, emulsion, powder, granule, oil, and so on. It is desirable that these various products be used properly depending on its purpose of use.

In preparing these formulations, the carrier to be used may be either solid or liquid. As those appropriate solid carriers, there may be enumerated: wheat bran; soybean meal, cellulosic powder, residue after extraction of plants, bark and other vegetative carries; and clay, talc, kaoline, bentonite, China clay, calcium carbonate, diatomaceous earth, silicic anhydride, synthesized calcium silicate, and other inorganic substances. As those appropriate liquid carriers, there may be enumerated: water; aliphatic hydrocarbons such as ligroin, kerosene, mineral oil, and so on; aromatic hydrocarbons such as benzene, toluene, xylene, methylnaphthalene, and so forth; chloro-hydrocarbons such as chloroform, dichloroethane, and so on; alcohols such as methanol, ethanol, i-propanol, n-butanol, and so on; ketones such as acetone, methylethyl ketone, cyclohexanone, and so on; nitrogen-containing organic solvents such as ethanol amine, dimethyl formamide, and so forth; and various others.

With a view to improving the properties of the formulations or increasing the biological effectiveness, it is also feasible to add various auxiliaries to the disinfectants for agricultural use according to the present invention. Examples are: various anionic or ionic surfactans; high molecular weight compounds such as sodium alginate, carboxymethyl cellulose, methyl cellulose, polyvinyl alcohol, gum arabic, gelatin, casein, and so on; sulfite pulp waste liquor, "DORILESS" (a tradename for a product manufactured and sold by Sankyo Co., Ltd., Japan), and so forth.

The disinfectant for agricultural use according to the present invention may contain therein various other active components which do not impair the preventive effect of the substance F-0368. Such active components are, for example: fungicide, insecticide, herbicide, acaricide, plant growth regulator, nematicide, bacteriocide, repellent, attractant, and so forth.

According to the present invention, there is also provided materials for agricultural use, containing therein the substance F-0368 and/or its salts. These agricultural materials can be obtained by mixing and blending the substance F-0368 and/or its salts with manure, culture soil for rice plant seedling, culture soil for horticultural use, manure for hydroponic cultivation, and so forth.

In order to sterilize the disease fungi in agriculture with use of the substance F-0368 according to the present invention, the substance F-0368 is incorporated in the above-mentioned disinfectants for agricultural use and materials for agricultural use, thereby killing the disease fungi in agriculture.

For preventing the diseases in agriculture by use of the substance F-0368, it is sufficient to carry out treatment by spraying and applying the substance F-0368 on the stems and leave of plants, or by absorption of the substance from the roots of the plants through soil irrigation.

In case the substance F-0368 is to be used for sterilization and prevention of diseases in agriculture, the substance may be used in its concentration of from 10 ppm to 5,000 ppm in general, or preferably from 100 ppm to 2,000 ppm, when the substance is to be sprayed on the surface of leaves.

In case the substance F-0368 according to the present invention is to be used for application to the nursery box and to the surface of water, concentration of the substance in the granule should be in a range of from 0.1% to 50%, or preferably from 0.2% to 20%.

The quantity of application of the above-mentioned granules may be generally in a range of from 30 g to 100 g per nursery box (having a dimension of 30×60×3 cm containing therein about 5 l of soil), and from 3 to 5 kg per 10 ares of paddy field.

As it is apparent from the foregoing explanations and will become evident from the preferred examples to follow hereinafter, the substance F-0368 according to the present invention is excellent in its disease preventive effect with a low dose: in particular, it has remarkable preventive effect against the blast disease and the bacterial leaf blight disease of the rice plant, with low toxicity to human being and animals, Accordingly, the disinfectant for agricultural use, the materials for agricultural use, the method for disinfecting the disease fungi and bacteria in agriculture, and the method for preventing diseases in agriculture according to the present invention are of great significance from the industrial standpoint. To add more, the substance F-0368 can be efficiently produced with the F-0368-substance-producing-microorganism which belongs to the genus Kitasatosporia.

In the following, it should be noted that the present invention is not limited to these examples and experimental examples alone, but it includes all possible embodiments which can be readily inferred from the findings as already described in the foregoing.

EXAMPLE 1

(Example of Producing Substance F-0368)

Figure 1:
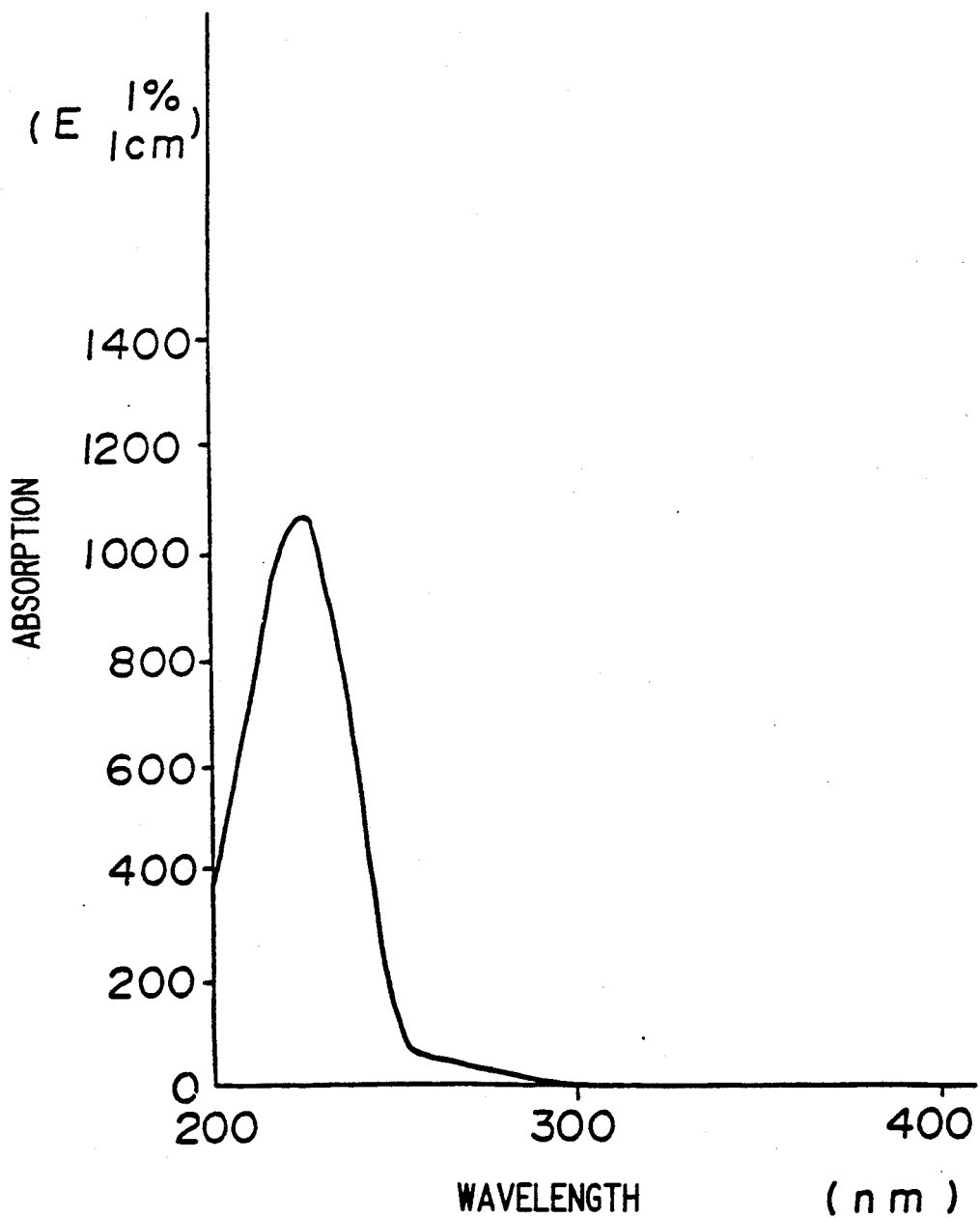
FIG. 1 shows an ultraviolet ray absorption spectrum of the substance F-0368 according to the present invention.
Figure 2:
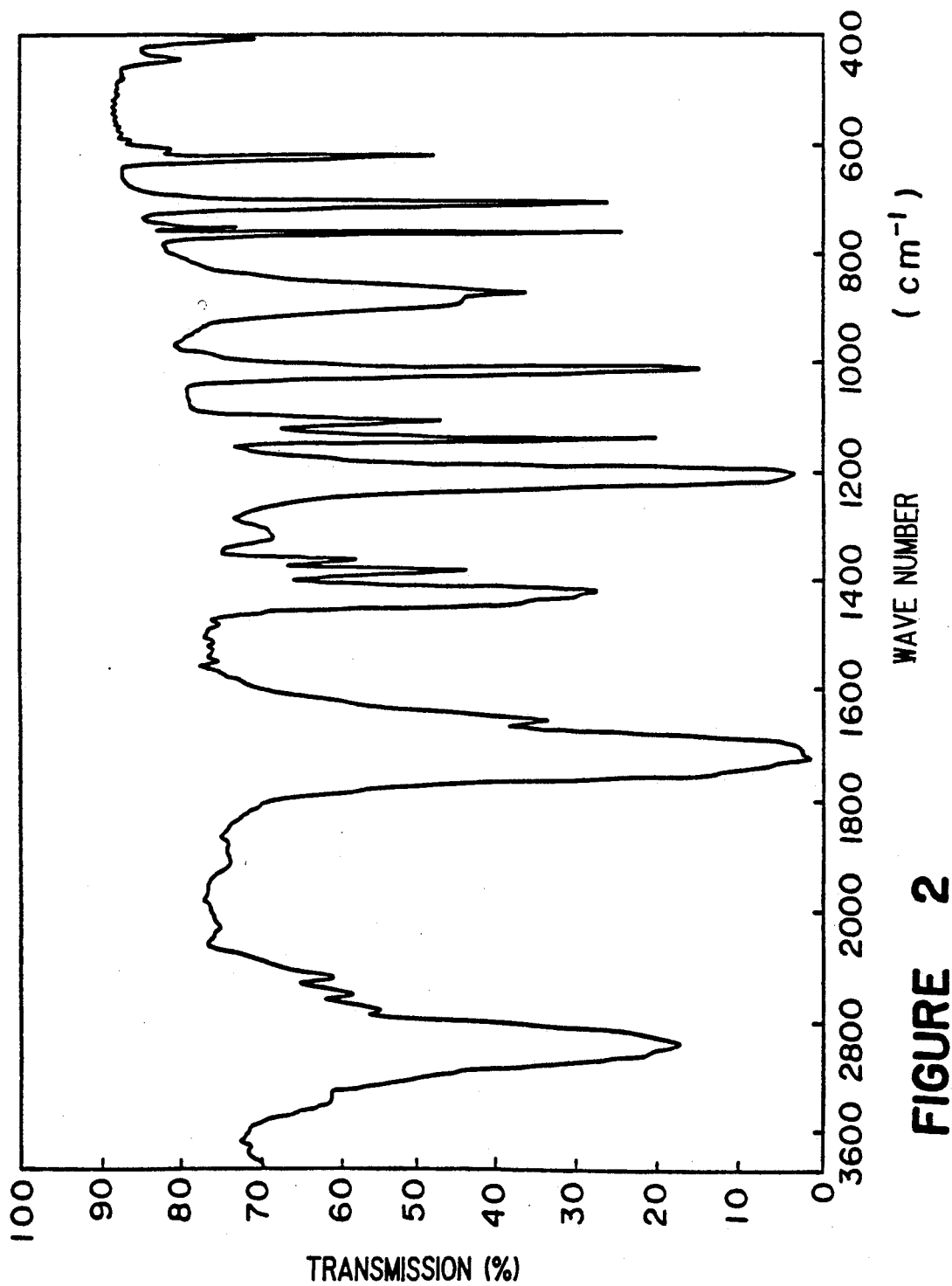
FIG. 2 shows an infrared ray absorption spectrum of the substance F-0368.

Culturing strain of microorganism Kitasatosporia sp. F-0368:

As the seed culture medium, use was made of the following composition: 1.5% of dextrin, 3% of starch, 1% of soybean meal, 0.3% of meat extract, 0.3% of polypeptone, 0.3% of yeast extract, 0.3% of calcium carbonate and 0.1% of sodium chloride (the medium having a pH value of 7.0 before sterilization).

70 ml each of the above-mentioned seed culture medium was separately taken into individual conical flasks, each having 500 ml capacity. Then, into each of these conical flasks, there was inoculated the strain of microorganism of Kitasatosporia sp. F-0368, followed by shaken culture for 72 hours at 28° C.

Subsequently, 1 l of this seed culture was transferred into a tank containing therein 100 l of production culture medium. This production medium was composed of: 1.5% of dextrin, 3% of starch, 1% of soybean meal, 0.3% of meat extract, 0.3% of polypeptone, 0.3% of yeast extract, 0.3% of calcium carbonate, 0.1% of sodium chloride, and 0.2% of antifoaming agent-CA-123 (the medium having a pH value of 6.5 before sterilization).

The culturing was conducted under aeration and agitation for 96 hours at a temperature of 28° C. The aerating quantity during the culturing was 100 l/min. and the number of revolution for the agitation was 200 r.p.m.

Isolation and collection of the substance F-0368:

After completion of the culture, the culture broth (having pH value of 8.4) was adjusted to have its pH value of 2.5 with hydrochloric acid, and then, as a filtration auxiliary, "Celite" (a tradename for diatomeceous earth and related products of Johns-Manvill Products Corp., U.S.A.) was added to the culture broth at a ratio of 4% for filtration. Subsequently, approximately 50 l of filtered culture liquid (pH value of 2.5) was subjected to extraction for two times with use of 50 l of ethyl acetate, after which the layer of ethyl acetate was concentrated under a reduced pressure, thereby obtaining approximately 180 g of dry solid substance containing therein the substance F-0368. This dry solid substance was further dissolved into a samll amount of ethyl acetate, and subjected to in a silica gel column which had been filled in advance with ethyl acetate to develop this solid substance with ethyl acetate, after which the active portion (about 1 l) was collected and subjected to extraction using 1 l of distilled water, after the pH value thereof had been adjusted to 8.0 with sodium hydroxide. In this way, the extracted active portion was transferred into distilled water (pH value of 8.0) completely. Furthermore, the distilled water was adjusted with hydrochloric acid to have its pH value of 2.0, and the dry solid substance was subjected to a column chromatograph (DIAION HP-20) having an adjusted pH value of 2.0 and the substance was developed with this acidic water (pH value of 2.0). Then, the active portion (approx. 1.5 l) was collected and subjected to extraction for two times with 1.5 l of ethyl acetate, after which the layer of ethyl acetate was concentrated under a reduced pressure, thereby obtaining approximately 18 g of white planar crystals of the substance F-0368.

EXAMPLE 2

5 ml of 3N-HCl aqueous solution was added to 150 mg (0.96 mM) of 3 methyl-4-methoxycarbonyl-2(5H)-furanone, and was stirred for three hours at a temperature of from 80° C. to 85° C. The reaction product was then extracted with ethyl acetate, and the solvent was fractionated under a reduced pressure. As the result, there was obtained an oily matter. Ethyl acetate-n-hexane was then added to the thus obtained oily matter to crystallize the same, whereby 110 mg of the substance F-0368 was obtained with a rate of yield of 80.9%.

In the following, there will be shown examples of the formulations of the disinfectants for agricultural use according to the present invention. It should, however, be noted that kinds of additives to the substance F-0368 and their mixing ratio are in no way limited to these examples alone, but changes may be made in a wide range.

EXAMPLE 3

Dusting powder 3 parts by weight of the substance F-0368, 2 parts by weight of talc and 55 parts by weight of clay were uniformly mixed in a mixer, and then the mixed material was pulverized to obtain dusting powder.

EXAMPLE 4

Water-dispersible powder 20 parts by weight of the substance F-0368, 5 parts by weight of wetting agent (alkylbenzene sulfonic acid type), 2 parts by weight of white carbon, and 73 parts by weight of clay were uniformly mixed in a mixer, and then the mixed material was pulverized to obtain water-dispersible powder.

EXAMPLE 5

Granule 20 parts by weight of the substance F-0368, 5 parts by weight of "TOXANON" (a tradename for a surfactant produced and marketed by Sanyo Kasei K.K., Japan), and 90 parts by weight of bentonite were granulated by the wet-type extrusion method, and then the granules were dried and sieved to obtain the desired grain size.

In the following, experimental examples will be presented for the tests conducted on the effectiveness and acute toxicity of the disinfectants for agricultural use according to the present invention.

EXPERIMENT 1

Test for preventing rice blast disease (test by spraying on leaves)

Water-dispersible powder containing the substance F-0368 prepared in accordance with Example 3 above was sprayed by use of a spray gun on rice plant (cv. "Nihonbare" at its 2 to 2.5 leaf stage), which was cultivated in a planting pot having a diameter of 9 cm, at a rate of 15 ml per pot. After lapse of one day from the spraying, spore suspension of the pathogenic fungus of this rice blast disease (i.e., *Pyricularia oryzae*) was inoculated on this rice plant by spraying, which was then placed in an humidity chamber at a temperature ranging from 24° C. to 26° C. and a relative humidity of 90% or above. After four days' passage, number of diseased leaf spots were counted to examine the preventive effect of the disinfectant. The results are shown in Table 2 below. It is to be noted that the value of preventive effect was calculated from the following equation.

Value of preventive effect =

$$\frac{\begin{pmatrix}\text{number of diseased}\\ \text{leaf spots in non-}\\ \text{treated plant}\end{pmatrix} - \begin{pmatrix}\text{number of diseased}\\ \text{leaf spots in}\\ \text{treated plant}\end{pmatrix}}{\begin{pmatrix}\text{number of diseased leaf spots}\\ \text{in non treated plant}\end{pmatrix}} \times 100(\%)$$

TABLE 2

|  | Quantity of Effective Component (ppm) | Value of Preventive Effect (%) |
|---|---|---|
| Water-dispersible powder containing the substance F-0368 of present invention | 100<br>500 | 70<br>75 |
| Non-treated | — | 0 |

As is apparent from Table 2 above, the substance F-0368 exhibits excellent preventive effect against the rice blast disease by spraying on the leaves.

EXPERIMENT 2

Test for preventing rice blast disease (test by application in nursery box)

50 g of the granule containing therein 1% of the substance F-0368, as prepared in accordance with Example 4 above, was uniformly scattered on rice plant (cv. "Nihonbare" at its 2.5 leaf stage) which was grown in a nursery box with a dimension of 30 cm long, 60 cm wide, and 3 cm high. After lapse of 24 hours fron scattering of the granule, young seedling was cut out together with soil (1×1×3 cm), and transplanted to a Wagner pot of 1/5000a with the soil having been attached to its root. After passage of 40 days from the transplant, spore suspension of *Pyricularia oryzae*, the pathogenic fungus of this rice blast disease, was inoculated by spraying on this young seedling, and then it was placed in an humidity chamber at a temperature of from 24° C. to 26° C. and a relative humidity of 90% or above, and kept therein. After lapse of seven days, number of diseased spot was counted to examine the disease preventive effect of the granular disinfectant. The value of preventive effect was calculated in the same manner as Experiment 1 above. The results of the experiment are shown in Table 3 below.

TABLE 3

|  | Quantity applied per nursery box (g) | Quantity of effective component as applied per nursery box (g) | Value of preventive effect |
|---|---|---|---|
| Granule containing 1% of F-0368 of this invention | 50 | 0.5 | 97 |
| Probenazole (granule containing 8% of effective component) | 30 | 2.4 | 95 |
| Isoprothyolan (granule containing 12% of effective component) | 75 | 9.0 | 90 |
| Non-treated | — | — | 0 |

As is apparent from Table 3 above, the substance F-0368 exhibits more excellent preventive effect than the conventional disinfectants in respect of the rice blast disease, by its application in the nursery box.

EXPERIMENT 3

Test for preventive effect of rice blast disease (test by application onto water surface)

Each of three kinds of granule containing therein 1%, 2.5% and 5%, respectively, of the substance F-0368 prepared in accordance with Example 3 above was uniformly scattered onto the rice plant (cv. "Nihonbare" at its fourth leaf stage) which has been grown in Wagner pot of 10000a (depth of water filling of 3 cm) from above the surface of water.

After lapse of seven days from scattering of the granule, spore suspension of *Pyricularia oryzae*, the pathogenic fungus of the rice blast disease was inoculated by spraying it onto this rice plant, which was then placed in an humidity chamber maintained at a temperature of from 24° C. to 26° C. and a relative humidity of 90%. After passage of seven days in the chamber, number of diseased leaf spots on upper two leaves of the rice plant was counted to examine the preventive effect by the granular disinfectant. By the way, the value of the preventive effect was calculated in the same manner as in Experiment 1 above. The results of the experiment are shown in Table 4 below.

TABLE 4

|  | Quantity of granule as applied per 10a (kg) | Quantity of effective component as applied per 10a (g) | Value of preventive effect (%) |
|---|---|---|---|
| Granule cont'ng 1% of F-0368 of this invention | 3 | 30 | 90 |
| Granule cont'ng 2.5% of same | 3 | 75 | 95 |
| Granule cont'ng 5% of same | 3 | 150 | 98 |
| Probenazole (granule containing 8%) | 3 | 240 | 95 |
| Non-treated | — | 0 | 0 |

As is apparent from Table 4 above, the substance F-0368 according to the present invention possesses more excellent preventing effect than the conventional disinfectants in respect of the rice blast disease, by its application onto the water surface.

EXPERIMENT 4

Test for preventive effect of rice bacterial leaf blight disease (test by application onto water surface)

Each of two kinds of granule containing therein 2.5% and 5%, respectively, of the substance F-0368 prepared in accordance with Example 3 above was uniformly scattered onto rice plant (cv. "Nihonbare" at its fifth leaf stage) which has been grown in the Wagner pot of 1/10000a (with depeth of water filling of 3 cm) from above the water surface.

After lapse of seven days from scattering of the granules, suspension of *Xanthomonas oryzae,* the pathogenic bacteria of this rice bacterial leaf blight disease, was inoculated by needle into the leaves, and the thus inoculated rice plant was placed in a green house. After passage of 20 days in the green house, length of the diseased lesion was measured to examine the preventive effect of the granular disinfectant. The results are shown in Table 5 below. By the way, the value of preventive effect was calculated by the following equation.

$$\text{Value of preventive effect} = \frac{\text{length of diseased lesion in non-treated plant} - \text{length of diseased lesion in treated plant}}{\text{length of diseased lesion in non-treated plant}} \times 100(\%)$$

TABLE 5

| | Quantity as applied per 10a (kg) | Quantity of effective component as applied per 10a (g) | Value of preventive effect (%) |
|---|---|---|---|
| Granule cont'ng 2.5% of F-0368 of this invention | 4 | 100 | 85 |
| Granule cont'ng 5% of same | 4 | 200 | 90 |
| Probenazole (granule cont'ng 8%) | 4 | 320 | 84 |
| Non-treated | — | — | 0 |

As is apparent from Table 5 above, the substance F-0368 according to the present invention also possesses excellent preventive effect against bacterial leaf blight disease of rice plant by its application onto the surface of water.

EXPERIMENT 5

Acute toxicity

Using JCL/ICR strain male mice (age: 5 weeks; weight: 28±1 g), a value of $LD_{50}$ (determined by their mortality after two weeks from commencement of administration into the peritoneal cavity) revealed that the amount of the chemical was approx. 200 mg/kg.

We claim:

1. A method for the production of substance F-0368 of the formula:

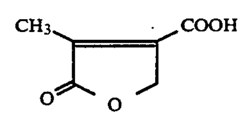

or salts thereof, comprising:

culturing Kitasatosporia sp. F-0368 in a culture medium; and then isolating and collecting said substance F-0368 from the culturing medium.

* * * * *